US011392194B1

(12) United States Patent
Kundra et al.

(10) Patent No.: US 11,392,194 B1
(45) Date of Patent: Jul. 19, 2022

(54) METHOD AND SYSTEM FOR DETECTING, INTERPRETING AND COMMUNICATING TOUCH, PHYSIOLOGICAL RESPONSES OR EMOTIONAL RESPONSES BETWEEN MOBILE USER DEVICES

(71) Applicant: Nextgen Capital Ventures, LLC, Alexandria, VA (US)

(72) Inventors: Monish Kundra, Washington, DC (US); Boris Bogatin, Philadelphia, PA (US)

(73) Assignee: Nextgen Capital Ventures, LLC, Alexandria, VA (US)

( * ) Notice: Subject to any disclaimer, the term of this patent is extended or adjusted under 35 U.S.C. 154(b) by 455 days.

(21) Appl. No.: 16/215,084

(22) Filed: Dec. 10, 2018

Related U.S. Application Data

(60) Provisional application No. 62/596,332, filed on Dec. 8, 2017.

(51) Int. Cl.
| | |
|---|---|
| *G06T 13/40* | (2011.01) |
| *G06F 3/0484* | (2022.01) |
| *A61B 5/16* | (2006.01) |
| *G06F 3/01* | (2006.01) |
| *A61B 5/02* | (2006.01) |
| *A61B 5/00* | (2006.01) |
| *H04L 65/1083* | (2022.01) |
| *H04L 65/1069* | (2022.01) |

(52) U.S. Cl.
CPC ............... *G06F 3/011* (2013.01); *A61B 5/02* (2013.01); *A61B 5/681* (2013.01); *G06F 3/016* (2013.01); *H04L 65/1069* (2013.01); *H04L 65/1083* (2013.01); *G06F 2203/011* (2013.01)

(58) Field of Classification Search
None
See application file for complete search history.

(56) References Cited

U.S. PATENT DOCUMENTS

| | | |
|---|---|---|
| 2008/0077489 A1 | 3/2008 | Gilley et al. |
| 2014/0025620 A1 | 1/2014 | Greenzeiger et al. |
| 2016/0058375 A1 | 3/2016 | Rothkopf |
| 2017/0011210 A1* | 1/2017 | Cheong .................. H04W 4/00 |

OTHER PUBLICATIONS https://www.techradar.com/news/wearables/how-to-send-your-heartbeat-with-apple-watch-1300884.
https://www.fastcompany.com/3044703/bringing-romance-to-the-apple-watch.
https://technewstube.com/engadget/863050/ai-equipped-apple-watch-can-detect-the-signs-of-a-stroke/.
https://www.inverse.com/article/13472-use-an-apple-watch-and-your-heart-rate-to-answer-the-big-question-am-i-in-love.
https://web.archive.org/web/20170925115143/http://www.shared-heartbeats.com/.
http://www.bitrebels.com/apps/app-captures-sound-your-heartbeat/.
https://www.theverge.com/2015/5/22/8639981/apple-watch-digital-touch-heartbeat.

* cited by examiner

*Primary Examiner* — Jon Eric C Morales
(74) *Attorney, Agent, or Firm* — Harness, Dickey & Pierce, P.L.C.

(57) ABSTRACT

A method includes initiating a session at a first device having a session identifier. The session being one-to many. The method further includes joining the session with a third device and a second device using a session identifier, generating a physical condition signal at a physical condition sensor, converting the physical condition signal to a first signal, communicating the first signal to the second device and third device through a network, and generating an (Continued)

indicator at the second device or the third device corresponding to the first signal.

27 Claims, 16 Drawing Sheets

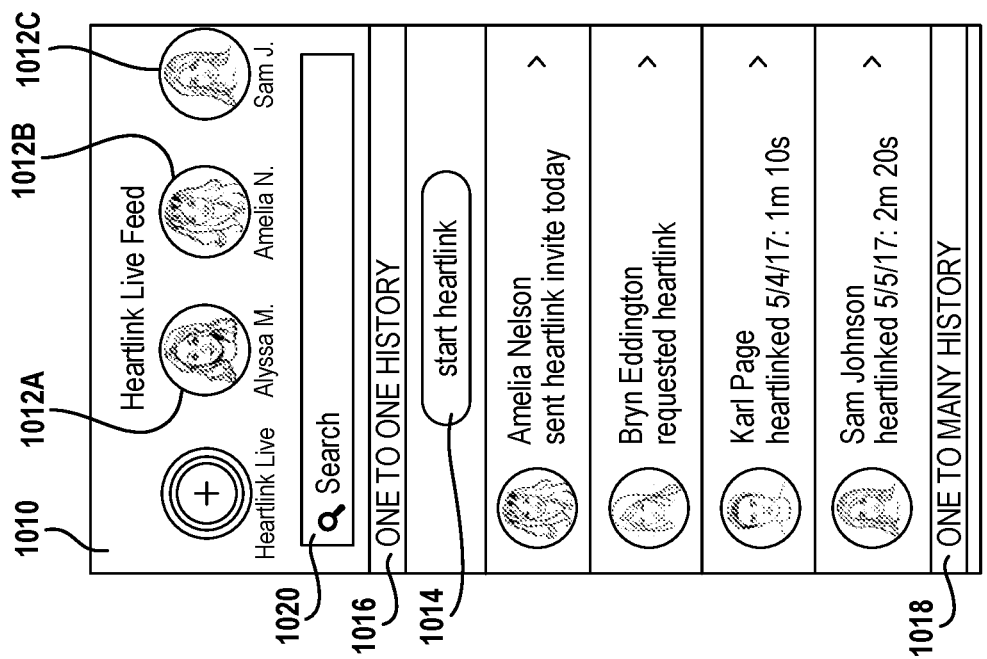
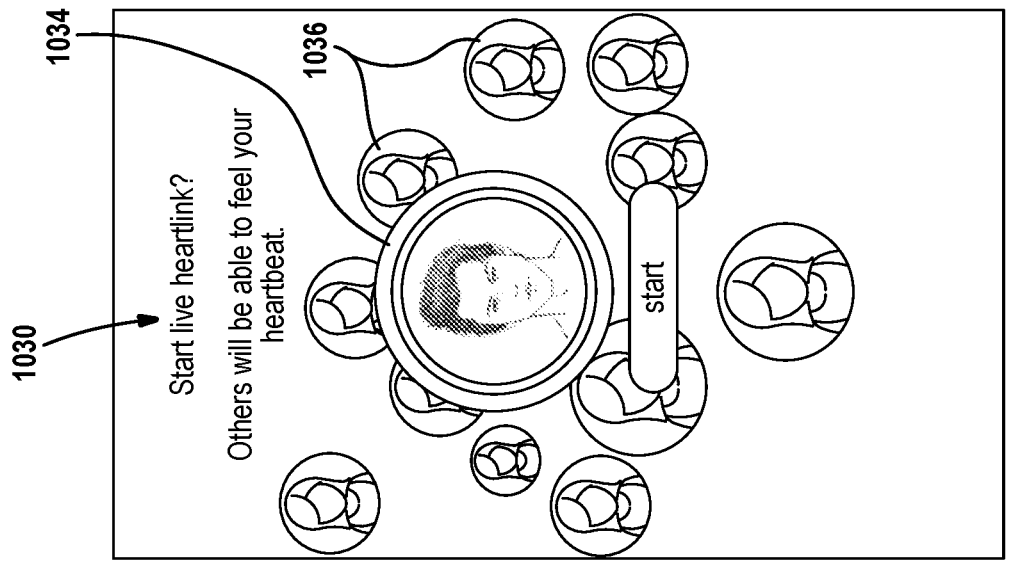
FIG. 10A
FIG. 10B

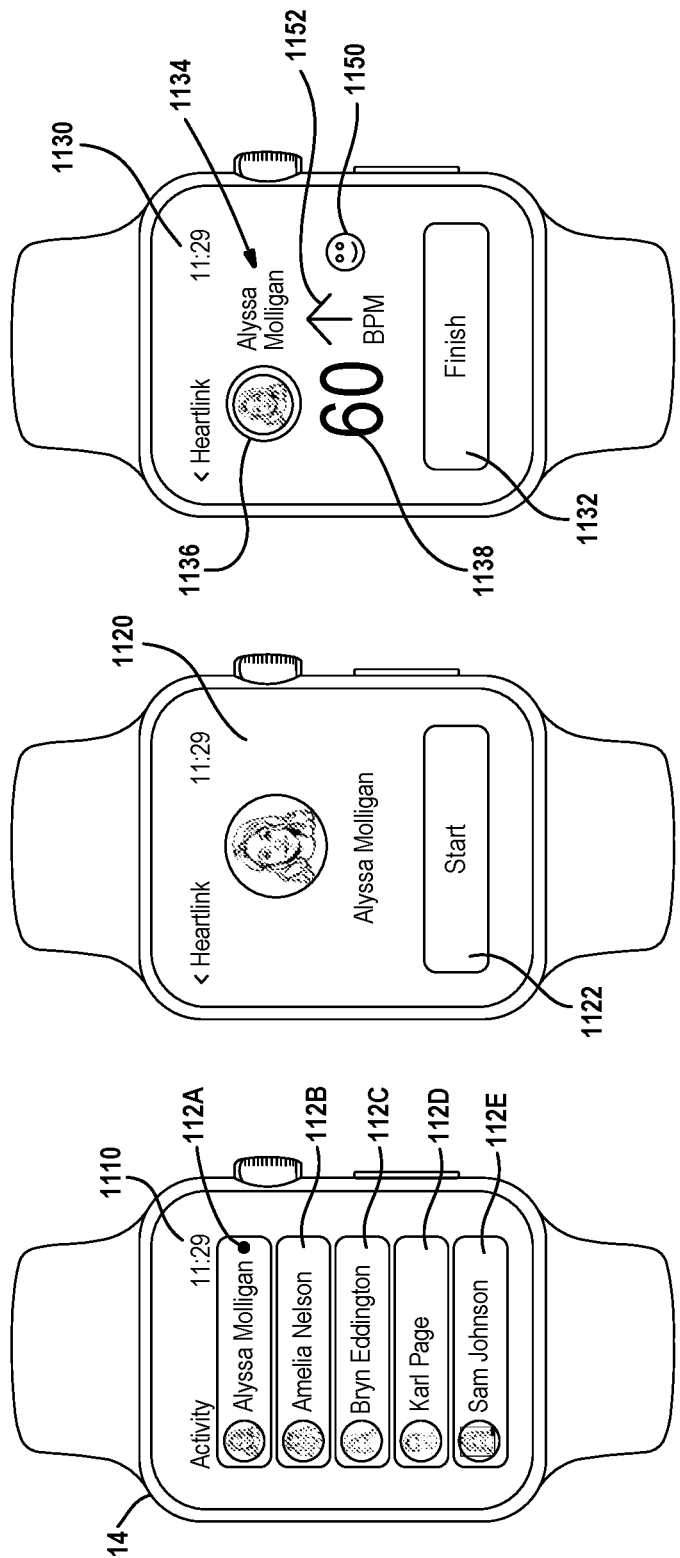

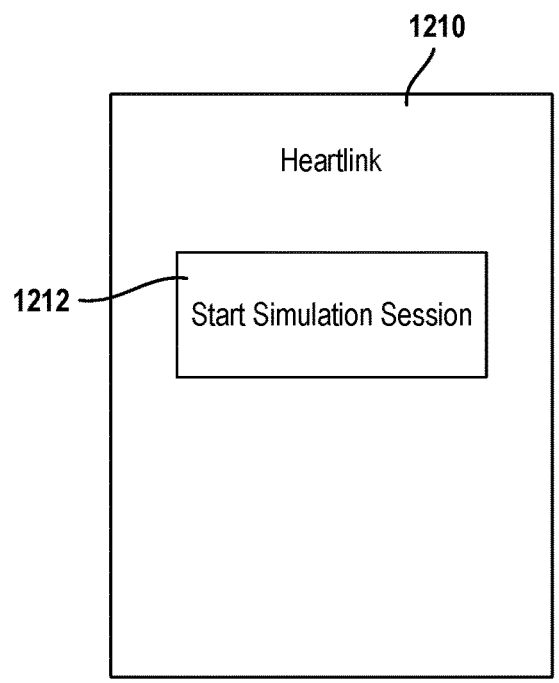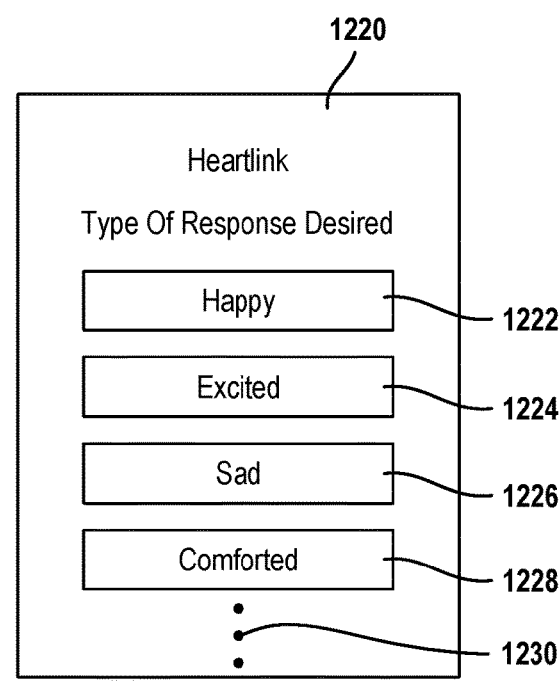
FIG. 12A     FIG. 12B

METHOD AND SYSTEM FOR DETECTING, INTERPRETING AND COMMUNICATING TOUCH, PHYSIOLOGICAL RESPONSES OR EMOTIONAL RESPONSES BETWEEN MOBILE USER DEVICES

CROSS-REFERENCE TO RELATED APPLICATIONS

This application claims the benefit of U.S. Provisional Application No. 62/596,332, filed on Dec. 8, 2017. The entire disclosure of the above application is incorporated herein by reference.

TECHNICAL FIELD

The present disclosure relates generally to electronically detecting physiological conditions and, more specifically, to a method and system for detecting, interpreting and communicating physiological response between mobile devices.

BACKGROUND

The statements in this section merely provide background information related to the present disclosure and may not constitute prior art.

With the advent of mobile phones, the world has become an even closer place. Mobile phones have become mobile computing devices and take the place of numerous devices from not that far in the past. Mobile phones allow one user to connect with another user by way of a conventional telephone call. Mobile phones also go well beyond the telephone aspect in that electronic communication such as texting and e-mailing are typically provided.

Mobile phones also allow some engagement between users in performing various activities like playing games, drawing pictures, and sending emojis, in order to allow a mutual exchange of expression.

One thing lacking in today's electronic communication is the actual feeling or the interpretation of the feeling of the other person in real time. Although emotions may be conveyed using emojis, a true feeling or the interpretation of the feeling of a person is not conveyed.

SUMMARY

The present disclosure provides a method for detecting physical characteristics and communicating signals of physiological or emotional characteristics corresponding to the physical factors between mobile devices.

In one aspect of the disclosure, a method includes initiating a session at a first device having a session identifier. The session being one-to many. The method further includes joining the session with a third device and a second device using a session identifier, generating a physical condition signal at a physical condition sensor, converting the physical condition signal to a first signal, communicating the first signal to the second device and third device through a network, and generating an indicator at the second device or the third device corresponding to the first signal.

In a further aspect of the disclosure, a method includes initiating a session at a first device, communicating a session identifier to a second device, joining the session from the second device, determining, at the first device, a first condition corresponding to a first physical condition, a first physiological condition, a first emotional condition or combinations thereof, converting the first condition to a first signal, communicating the first signal to the second device through a network, receiving the first signal at the second device, generating a first indicator at the second device corresponding to the first signal, determining, at the second device, a second condition corresponding to a second physical condition, a second physiological condition, a second emotional condition or combinations thereof in response to the first indicator, converting the second condition to a second signal, communicating the second signal to the first device through the network, receiving the second signal at the first device, and generating a second indicator at the first device corresponding to the second signal.

In yet another aspect of the disclosure, a method includes initiating a session at a first device, communicating a session identifier to a second device, joining the session using the second device, selecting a desired response to ellicit from a second user of a second device of the first device to form a selection signal, converting the selection signal into a first signal corresponding to a physical condition, a physiological condition, an emotional condition or combinations thereof based on the desired response, communicating the first signal to the second device through a network, and generating an indicator at the second device corresponding to the first signal.

In another aspect of the disclosure, a method includes initiating a session at a first device, communicating a session identifier to a second device, joining a session using a second device, determining, at the second device, a first condition corresponding to a first physical condition, a first physiological condition, a first emotional condition or combinations thereof in response to a first input, converting the first condition to a first signal, communicating the first signal to the first device through a network to a server associated with the session, receiving the first signal at the server device, and performing an action at the server device in response to the signal.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 10A is a screen display for providing a live session.

FIG. 10B is a screen display for finishing the initiation of a live session.

FIG. 11A is a screen display for initiating a session with a particular user from a companion device.

FIG. 11B is a screen display for starting a session.

FIG. 11C is a screen display for the session started in FIG. 11B.

FIG. 12A is a screen display for starting a simulation session.

FIG. 12B is a screen display for selecting a desired response from another user.

DETAILED DESCRIPTION

Figure 1:
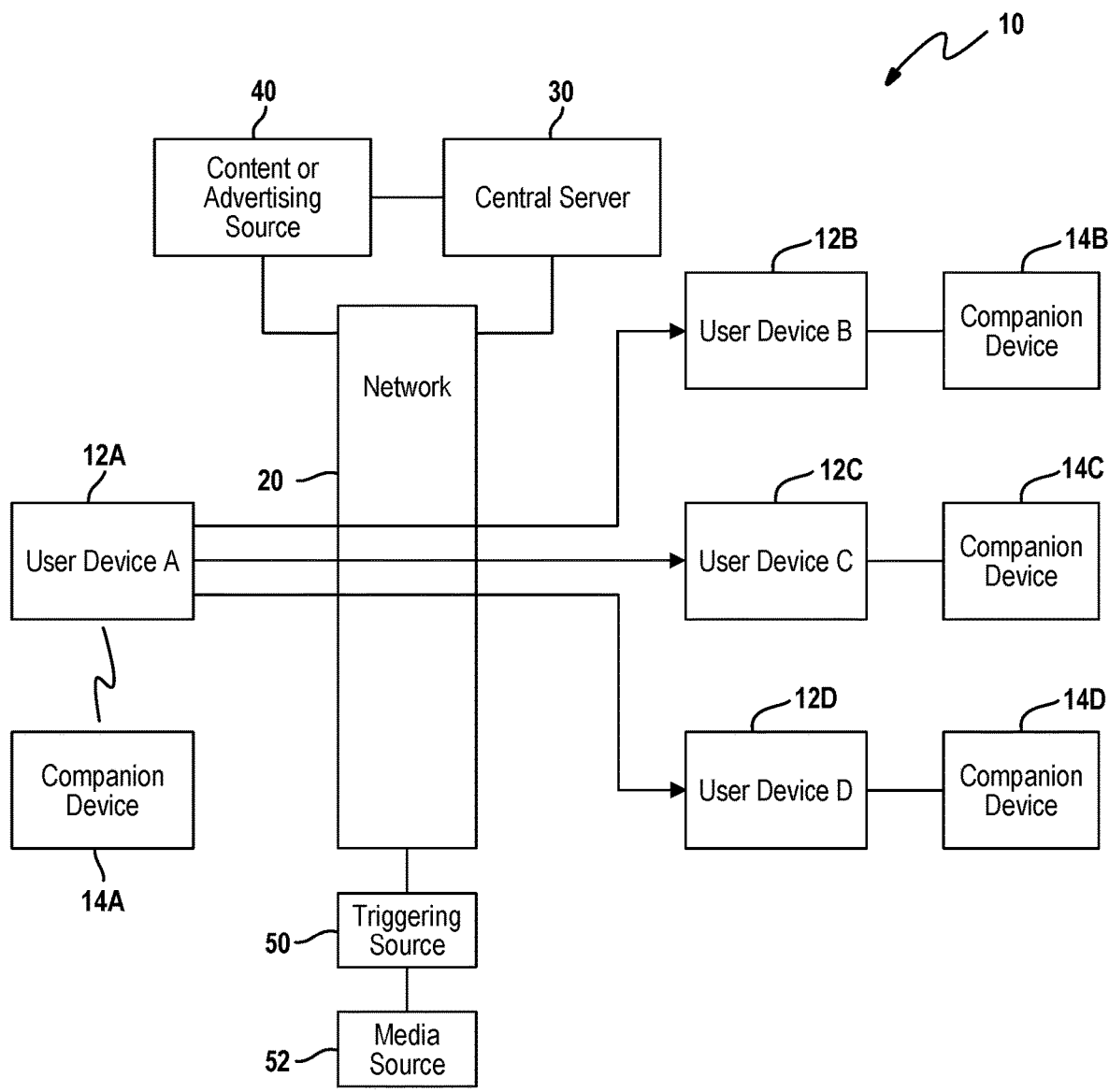
FIG. 1 is a block diagrammatic view of a system according to the present example.

The following description is merely exemplary in nature and is not intended to limit the present disclosure, application, or uses. For purposes of clarity, the same reference numbers will be used in the drawings to identify similar elements. As used herein, the term module refers to an application specific integrated circuit (ASIC), an electronic circuit, a processor (shared, dedicated, or group) and memory that execute one or more software or firmware programs, a combinational logic circuit, and/or other suitable components that provide the described functionality. As used herein, the phrase at least one of A, B, and C should be construed to mean a logical (A or B or C), using a non-exclusive logical OR. It should be understood that steps within a method may be executed in different order without altering the principles of the present disclosure.

The teachings of the present disclosure can be implemented in a system for electronically communicating content to an end user or user device. The user device may be formed using a general computing device having a memory or other data storage for incoming and outgoing data. The memory may comprise but is not limited to a hard drive, FLASH, RAM, PROM, EEPROM, ROM phase-change memory or other discrete memory components.

Each general purpose computing device may be implemented electronically in analog circuitry, digital circuitry or combinations thereof. Further, the computing device may include a microprocessor or microcontroller that performs instructions to carry out the steps performed by the various system components.

Referring now to FIG. 1, a system 10 includes a plurality of user devices 12A, 12B, 12C and 12D (individually 12). In this example each user device 12 includes a companion device 14A, 14B, 14C and 14D (individually 14). Although each of the user devices 12A-12D have a respective companion device 14A-14D as illustrated, a companion device 14 is not required as will be described in more detail below. A companion device 14 may be used without the associated user device 12.

The user devices 12A-12D may comprise a cellular or other type of computing device. The user device 12A may be in direct communication with the corresponding companion device 14 using localized communication such as Bluetooth®. Of course, direct communication between the user device 12 and the user device 14 may take place using a cable or wired connection.

Each of the user devices may be in communication with each other through a network 20. The network 20 is illustrated as a single box but represents various types of networks including a cellular network, an internet, a cable network, a public switched telephone network (PSTN), a satellite communication network and the like. The network 20 may be a combination of wired and wireless systems, terrestrial and extra-terrestrial that are used for communicating electronic signals between the various user devices 12A-12D.

The user devices 12A-12D may also be in communication with a central server 30. The central server 30 is described in more detail below. In general, the central server may be a service provider for providing or exchanging electrical signals having data corresponding to physical, physiological or emotional conditions of a user of one of the user devices. The server 30 may represent one or more servers, which may be in a same or physically different location. Server 30 may simulate a first server as described below. As will be described in more detail below, the user devices 12A-12D and/or the companion devices 14A-14D may detect physical conditions, physiological conditions, or emotional conditions and convert the condition to electrical signals or electrical data signals that are a digital representation of the respective physical condition, physiological condition, or emotional condition. The physical condition, physiological condition, or emotional condition may be referred to as a physical data signal, physiological data signal, or emotional data signal Examples of user devices 12 include but are not limited to cellular telephones, mobile devices, laptop computers or table computers. The companion device 14 may, for example, include wearable devices such as a watch or Google Glass® type device, and is in communication with the user device 12 or may act alone. That is, the user device 12 may also include a watch, Google Glass® or other type of wearable device capable of communicating with the network 20.

The system 10 may also include a content or advertising source 40. The advertising source 40 may be in communication with the central server 30 or may be in direct communication with the network 20. As will be described in more detail below, the content or advertising source 40 may provide content or advertising to various user devices 12A-12D or companion devices 14A-14D in response to received input such as physical, physiological or emotional signals received from the user devices 12A-12D and the companion devices 14A-14D.

A triggering source 50 may also be in communication with a network 20. A triggering source 50 may provide feedback or timing for various types of signals from the user devices and companion devices. For example, the triggering source 50 may be, but are not limited to a movie, television program or sporting event. As will be described in more detail below, responses from users of user devices 12A-12D or companion devices 14A 14B may be monitored and provide to influence such things as advertising from the advertising source, changing displays of the user devices 12A-12D or companion devices 14A-14D or changing playback of a movie or television show. The triggering source 50 may be in communication with a media source 52 to provide different types of content to the users through the network 20. The media source 52 may also directly provide media or content to the user devices through a different manner outside of the network. For example, the media source may communicate television or movies through a conventional video distribution service while the central server 30 monitors the timing due to the initiation of a session. The triggering source 50 and the media source 52 are illustrated as coupled to the network 20. However, the triggering source 50 and the media source 52 may be in communication directly with the network 20 or may be connected through central server 30. Details of the aspects of the intercommunication of the elements set forth in the system 10 are provided below.

Figure 2:
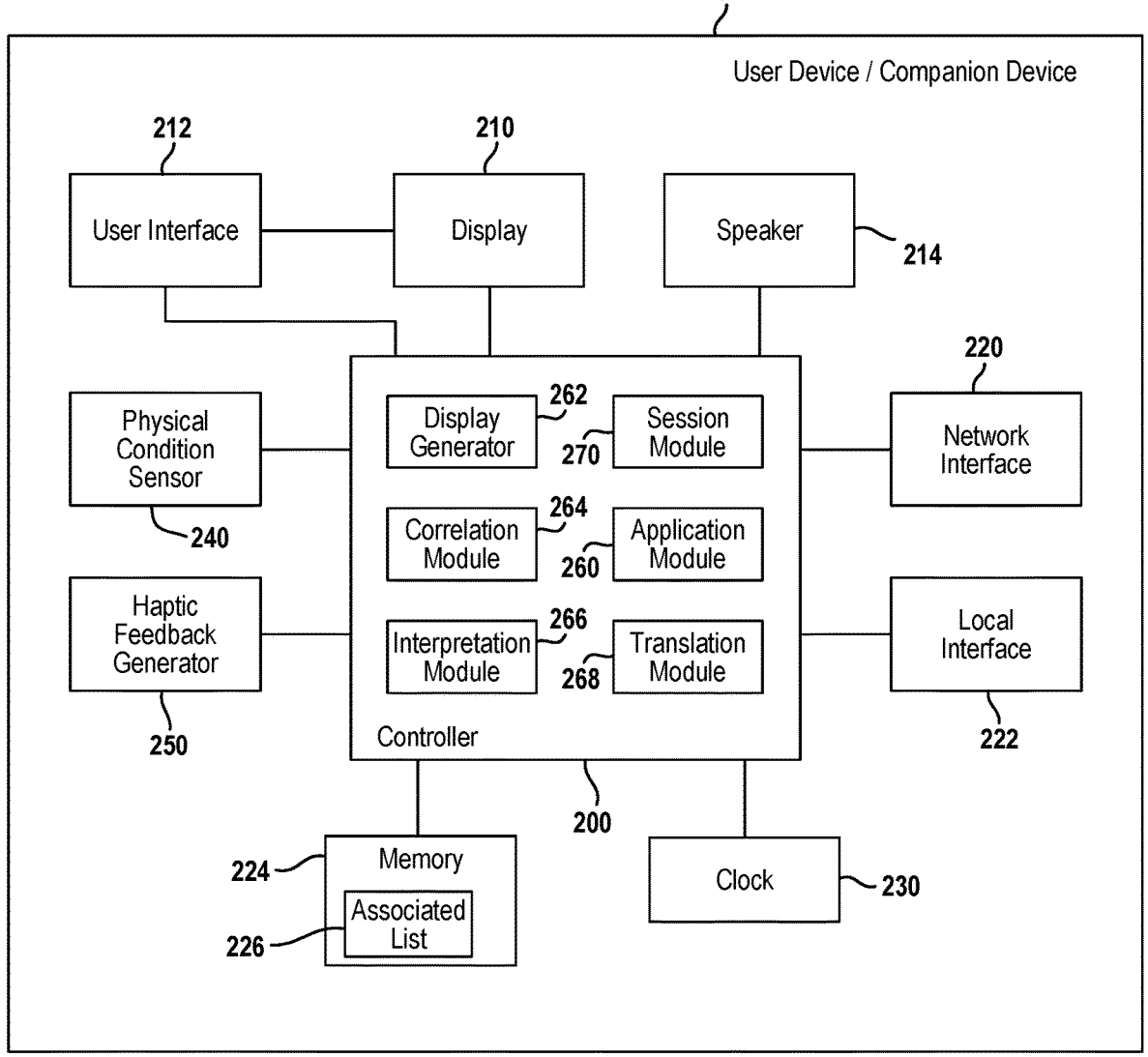
FIG. 2 is a block diagrammatic view of a user device or companion device.

Referring now to FIG. 2, a user device 12 is illustrated in further detail. User device 12 includes a controller 200. The controller 200 performs various functions and is in communication with various modules within the user device 12. The controller 200 may be used for controlling a display 210. The display 210 may be but is not limited to an LCD display or an OLED display. The display 210 may be a touchscreen and thus provide the function of a user interface 212. The user interface 212 may also include separate buttons which may be virtual buttons displayed on the display 210 or actual physical buttons or keypad on the device for providing various inputs and making various selections. The user interface 212 generates selection signals and may also be used for entering letters, numbers and symbols.

The controller 200 may also be in communication with at least one speaker 214. The speaker 214 generates an audible response to an audio signal communicated from the controller 200. The audio response may be a voice signal or other type of audible response.

The controller 200 may also be in communication with a network interface 220. The network interface 220 may provide intercommunication with one or more different types of networks. The network interface 220, may, for example, be in communication with a cellular network, a satellite network, an RF network or other types of networks.

The controller 200 may also be in communication with a local interface 222. The local interface may be a wired or wireless connection for coupling the user device 12 to a companion device. The local interface 222 may be a Bluetooth® interface.

The controller 200 may also be in communication with a memory 224. The memory 224 may be used for storing various parameters, settings and other data for operating the user device. One type of data that may be stored within the memory is an associated list 226. The associated list 226 may provide a list of friends, relatives or other groups of users that the user device regularly communicates. For a celebrity, users may subscribe to their favorite celebrity's associated list. Identifiers and addresses may also be stored within the associated list 226.

A clock 230 may also be in communication with the controller 200. The clock 230 may provide timing of signals such as the timing or period for heartbeat signals. The clock 230 may also provide an actual time corresponding to the time of day. The clock 230 may be synchronized with a clock received through the network interface 220. The clock 230 may also be used for timing a session and generating a corresponding signal therefor.

The controller 200 may also be in communication with a physical condition sensor 240. The physical condition sensor 240 may be one or more sensors used to sense different physical conditions of a user of the user device. The physical condition sensor 240 may be a separate touch pad or one or more types of discreet sensors for sensing various types of physical conditions. The physical condition sensor 240 may be within the device or on the outer surface to touch the skin of the user. For example, the heartbeat of the user may be sensed by the physical condition sensor 240 being a heartbeat sensor. The temperature of the user may also be sensed by the physical condition sensor 240. A galvanic response signal may also be generated by the physical condition sensor 240. The heart rate intensity and blood pressure may also be determined by the physical sensor. For a heartbeat signal, various types of cellular phones include a health monitoring system such as the Health Kit® by Apple®. The physical condition sensor signals generated by the physical condition sensor 240 may correspond to or may be interpreted individually or collectively to physiological or emotional conditions of the user device. The physical condition sensor 240 may also be a sweat rate sensor or a capacitive sensor.

A haptic feedback generator 250 may also be in communication with the controller 200. The haptic feedback generator 250 may generate haptic feedback to the user. The haptic feedback generator 250 may provide vibrations, pulses or other types of physical responses at the user device 12. For example, the haptic feedback generator 250 may generate vibrations corresponding to the heartbeat of another as received within the user device 12. The haptic feedback generator may also generate signals corresponding to touch. That is, light touches or hard touches may be simulated within the haptic feedback generator 250. The haptic feedback generator 250 may also include but correspond to temperature generator, galvanic generator, and touch intensity generator.

The controller 200 may include various modules for performing different functions. For example, the controller 200 may include an application module 260 used for running an application such as the "Heart Link" application that starts a session will be described below. The application module 260 may be used for running more than one application simultaneously.

The controller 200 may also have display generator 262 used for displaying data at various locations on the display 210. The display generator 262 may also be used for generating portions of the user interface 212. That is, the user interface 212 may be implemented in touchscreen buttons generated by the display generator 262.

A correlation module 264 may be used to correlate a desired response to an actual response. As will be described in more detail, when a physical signal corresponding to a physiological or emotional signals communicated another user to elicit a particular response the physical condition, physiological condition or emotional condition signals received back from the first user may be correlated to see how well the desired response corresponds to the actual response from the other user. The correlation module 264 may store the correlation and may store the data associated therewith within the memory 224 so that future signals generated from the user device 14 may elicit a closer or actual response to the desired response. As such, this may be an iterative process. This will be described in more detail below.

The controller 200 may also include an interpretation module 266. The interpretation module 266 may be used to interpret the physical signals received from a first user or another user and, in conjunction with the display generator 262 are used to generate an indicator or a display 210. The interpretation module 266 may generate an interpretation of physical condition signals into a physiological condition signal or an emotional condition signal. The signals each contain data. The interpretation module 266 may also interpret the physical condition signal together with other user inputs such as those from the user interface. For example, inputs may be provided to confirm or help narrow the physiological condition or emotional condition of the user of the first device. The interpretation may be arrived at as a result of the physical expression of a first user matching a previously identified pattern, as a result of the application recording a series of physical expressions of a first user, including over time, to come up with its interpretation, and/or as a result of the application learning that users with certain physical expression patterns are undergoing a certain physiological or emotional state (ie. sadness) and interpreting that the first user is also undergoing the same physiological or emotional state based on the patter of the first user's physical expression. The process may use artificial intelligence to learn reactions over time based on response signals and the correlation o the intended reaction.

The controller 200 may also include a translation module 268. The translation module 268 may be used for translating the signals from the physical sensor 240 at the end of the user device to electrical signals for communicating to other user devices.

The user device 12 illustrated in FIG. 2 may also correspond directly to a companion device 14. That is, the companion device 14 may include the same feature but may be packaged in a different type of package such as a watch or eyewear, as mentioned above. Thus, the companion device 14 will not be described in detail.

The controller 200 may also include a session module 270. The session module 270 is used for forming a session between a first user device and one or more user devices. The session module 270 may use a URL or another type of address for intercommunicating signals to another user device. The session module 270 may facilitate the signals to be interpreted, the signals to be translated and intercommunicate them with various users.

Figure 3:
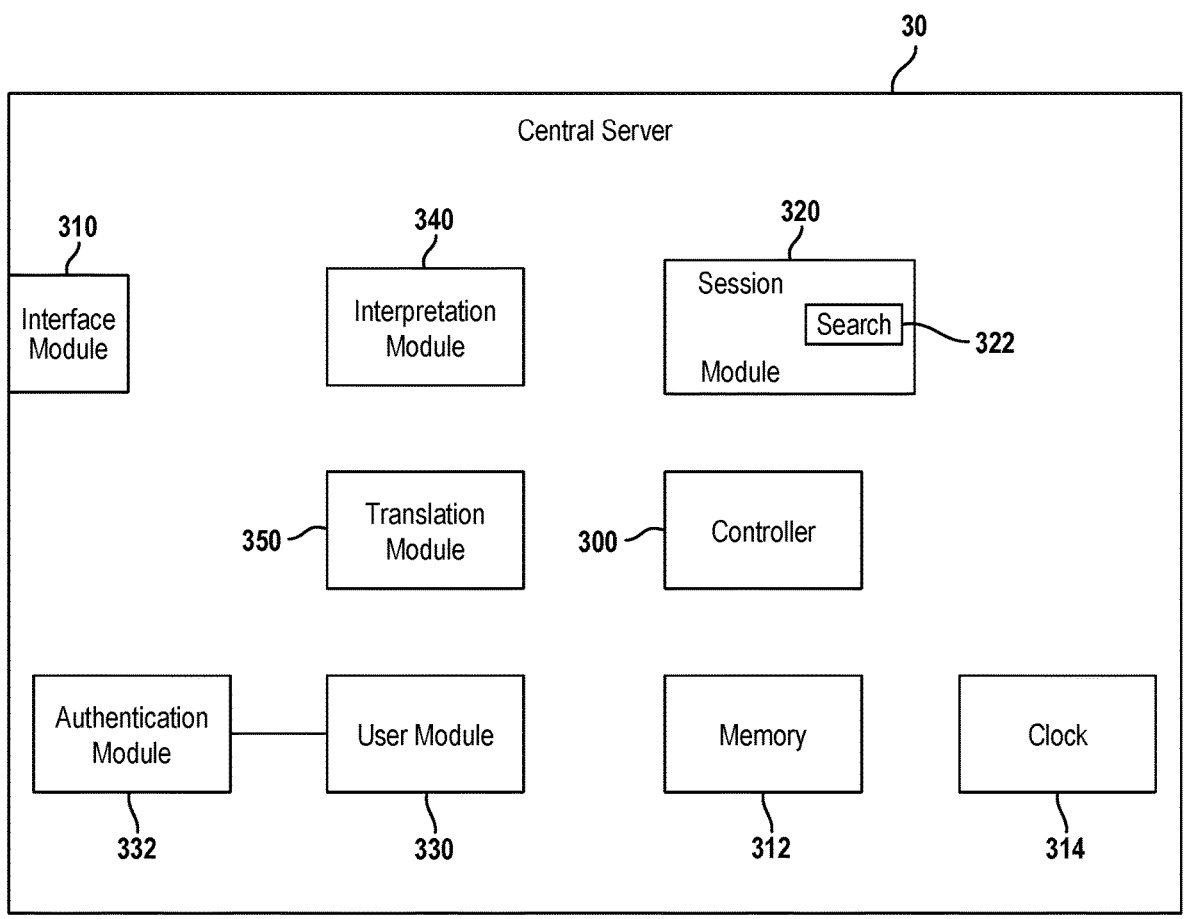
FIG. 3 is a block diagrammatic view of a central server.

Referring now to FIG. 3, the central server 30 may include a controller 300. The controller 300 controls various functions and intercommunications within the central server 30 as well as communications outside the central server 30. The controller may be in communication with an interface module 310. The interface module 310 is used to communicate with the network 20 illustrated in FIG. 1. The interface module 310 may be configured to communicate with various types of networks such as those in conjunction with FIG. 1.

The controller 300 may be in communication with a memory 312 which is used for storing various data used for forming sessions, user data, network data and the like. A clock module 314 may also be in communication with the controller 300. The clock module 314 may be used for timing various sessions and triggering time outs the like due to the lack of intercommunication within a various time. The clock 314 may be a standard time unit or may be a count up or count down timer as well.

The central server 30 may include a session module 320. The session module 320 may be used to form sessions between various users and keep track of various sessions between various users. The session module 320 may be used to establish sessions by using a search module 322 that is used for searching for other types of sessions such as live sessions for which a user may join.

The central server 30 may also include a user module 330 that is used to store data regarding the various users. For example, the user module 330 may store addresses of the users so that communication signals may be directed thereto. The user module 330 may be in communication with an authentication module 332. To establish a session and intercommunicate with other user devices, a first user device may require authentications such as providing a password, a control word or the like. The authentication module 332 along with the user module 330 may allow the intercommunications to take place. Once a particular user has been authenticated a session may be established. The session module 320 may thus allow various authenticated users to intercommunicate.

The central server 30 may also include an interpretation module 340. The interpretation module 340 acts in a similar manner as that set forth in the user device 12. That is, the interpretation module 340 may interpret the received signals from the user device 12 or companion device 14. That is, physical, physiological or emotional condition signals may be received from a user and, rather than performing an interpretation at the user device 12 interpretation may be performed within the central server at the interpretation module 340. Thus, the output of the interpretation module may be a particular screen display or haptic control signal that is ultimately communicated to another user device. In certain situations "slim" user devices may be used and thus the computing power may be limited especially when a high number of signals from a user device are interpreted. By interpreting the signals from the user device 12 at the central server 30, the final result and thus network latency and processing latency may be reduced.

The central server 30 may also include a translation module 350. The translation module 350 may be used to translate the interpreted signals into a signal suitable for communication through the interface module 310 and the network 320. That is, the format of the signal may change.

Figure 4:
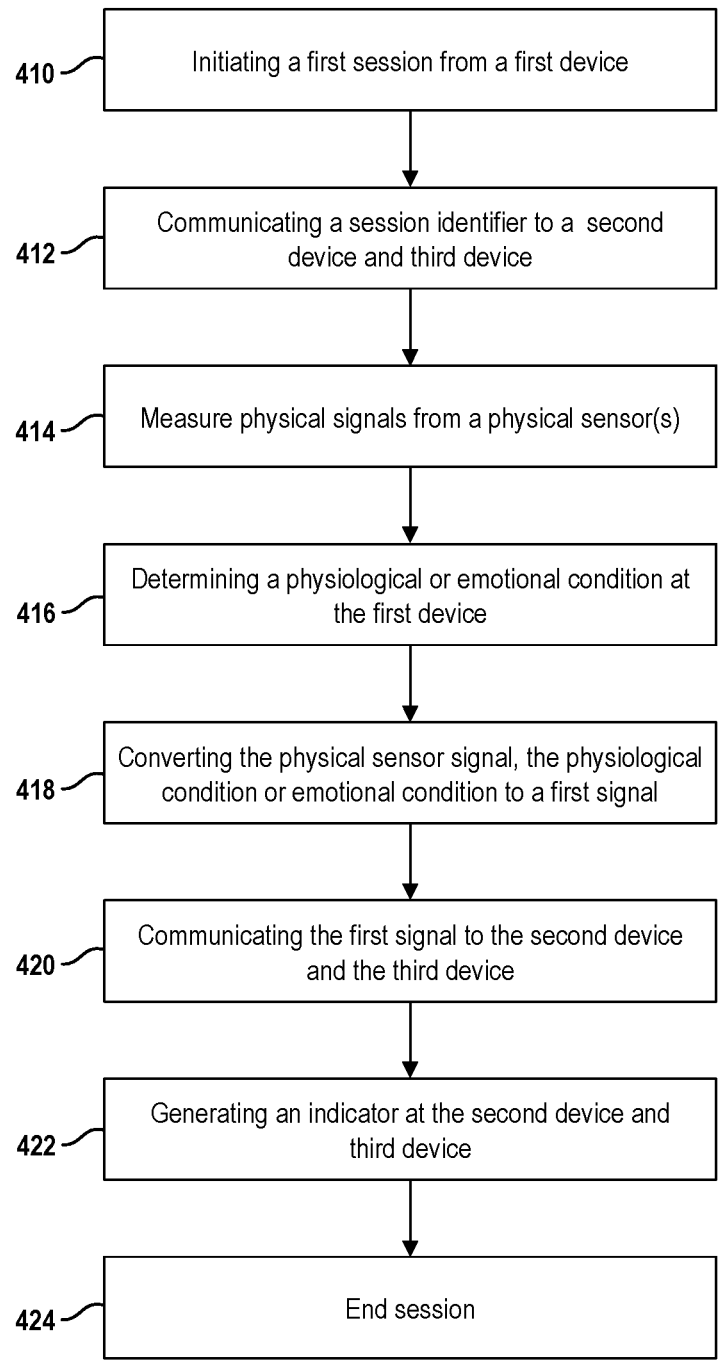
FIG. 4 is a flowchart of method for initiating a session.

Referring now to FIG. 4, a method for relaying a heart rate or other emotional or physiological conditions to another user device is set forth. In general, an expression of a "touch" is communicated from one user device to a plurality of user devices. The "touch" may be one or more of a physical signal, a physiological signal or an emotion signal. It should be noted that although a first user device is described as being in communication with a second and third user device, various numbers of user devices may be interconnected. Further, the sharing of data may be linked to various types of activities such as a reality TV show, a Facebook Live session, or even a movie. Underlying such activities is the establishment of a session. In step 410, a first session from a first device is initiated. The initiation may take place at a downloaded application stored within the user device 12 and/or companion device 14 as described above. The initiation of a first session may be performed from the user device 12 or the companion device 14. Screen displays illustrating the process are set forth below. In step 412 a session identifier may be formed during the initiating of a session set forth in step 410. The session identifier may be communicated to one or more user devices such as a second device and a third device. By communicating a session identifier the second device and third device may join the session as described in more detail below. The session identifier may be communicated to the second and third device in various ways. An audible signal, a text message, an e-mail, a direct notification from the application to the application of the second device and third device, a push notification or the like.

In step 414 physical signals are measured from one or more physical sensors within the first device. For example, a heartbeat signal may be measured. Other types of signals from the same or different sensors may include a galvanic response signal, a heart rate intensity signal and other types of physical sensors may be used as mentioned above. In step 416 a physiological or emotional condition may also be determined at the first device. The physical signal plus other user inputs may be interpreted into a physiological or emotional condition. The interpretation may be an option as the physical signals themselves. As mentioned above, the interpretation may provide various types of data or indicators. As will be described in more detail below emojis or other types of symbols as well as data from the physical sensors may be communicated to the second and third device. As mentioned above, the user device may include a translation module to translate the signals into a first signal formatted for communicating to other devices. The first signal may be a physical, physiological or emotional condition. The communicated signals allows a haptic feedback generator or another indicator on another user device to play back or indicate a heartbeat or physiological or emotional condition. Thus, the first signal may include data corresponding to physiological or emotional conditions as well as electrical signals that correspond directly to a heartbeat at the first device. Step 418 converts the physical, physiological or emotional signal into the first signal. In step 420 the first signal is communicated to the second device and the third device. The first signal is communicated through the network 20 of FIG. 1 through the various devices. As mentioned above, the network 20 may be comprised of a plurality of networks including wired and wireless networks and terrestrial and extra-terrestrial networks as well. Ultimately an indicator is generated at the second device and the third device in response to the first signal. The indicator generated at the second and third device may be one of a number of types of signals. A screen display, a haptic feedback generation, a discreet indicator or indicator may all be used to generate the indicator. A screen indicator displayed on a touchscreen is set forth below.

In step 424 the session is ended at the first user device. That is, the first user device may terminate the session by a screen display or the like. When the session ends, the remaining user devices within the session also have their session terminated. That is, the session does not continue after the first user terminates or ends the session.

Figure 5:
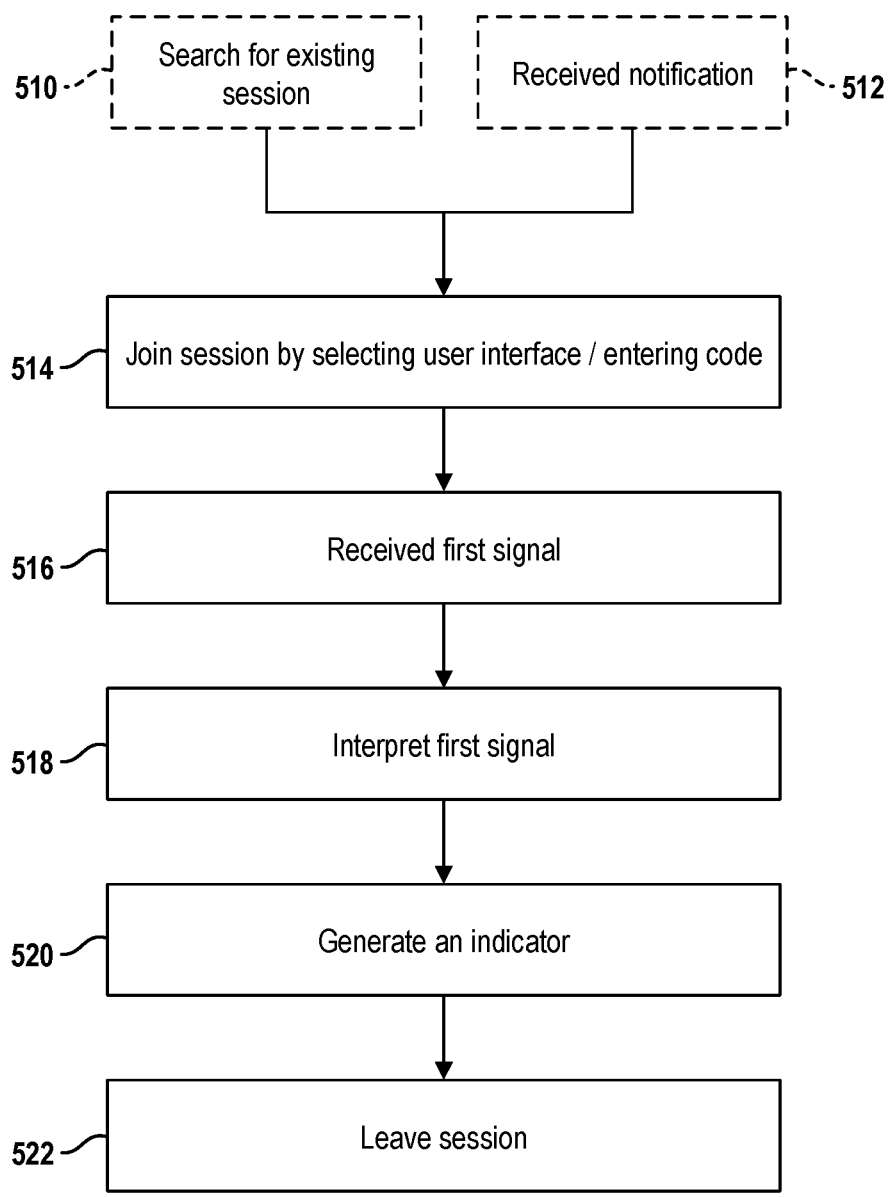
FIG. 5 is a flowchart of a method for joining a session.

Referring now to FIG. 5, a method of operating the second and third device is set forth. In FIG. 5, other devices may join a session in various ways. In step 510, a session may be searched for after receiving a session identifier such as that communicated in step 412 above. The existing session may have a link or other type of address or "identifier' for accessing a live session to receive the data from the first device.

In step 512 an alternative to searching for an existing session may be performed. A notification may be received directly for the first device at the second and third device. The notification may include a session identifier and other types of identifying features such as a picture or accompanied text. The notifications may be directed to a second and third device whose owners may be friends, family or fans. Notifications that include a session identifier may be received by voice such as over a loud speaker or speaker of the user device, through a television, radio, social media platforms such as Facebook or Twitter or through direct messaging or e-mails. Presumably, other user devices have the application on their respective devices.

In step 514 a session is joined by selecting the session on a user interface or entering a code. As will be illustrated below, a screen display with related or preselected users may be displayed on the screen display of the user device. A selection may take place by touching the appropriate session or picture associated with the session on the screen display. In step 516 a first signal is received from the first device at the second and third device. In step 518 the physical signal may be interpreted to physiological or emotional signals. In step 520 an indicator corresponding to the first signal is generated at the second and third user device. The indicator, as mentioned above, may be haptic feedback generated at a haptic feedback generator. The haptic feedback may correspond to the heartbeat of the first user (based on the physical signal). The indicator may be generated on a screen display such as an emoji. The screen display may also generate an indication as to the intensity of the heartbeat signal. That is, the beats per minute and the intensity of each beat may be generated at the screen display. Thus, numerical values may be displayed or indicated to the second and third user as well as sounds and visual signals on the screen display. The screen display may also generate a time that the heart link session has been activated. An indicator may also be provided as to the time that the present user has been linked to the first device.

In step 522 the second device or third device may leave the session. Leaving the session at the second or third device or other devices may not affect the ongoing session.

In operation, FIGS. 4 and 5 are useful in many one-to-many activities like a reality television show, Facebook live sessions, movies, an exercise class or sporting event. Celebrities or television stars may wear or transmit physical, physiological or emotional signals to make the audiences feel more a part of the event.

Figure 6A:
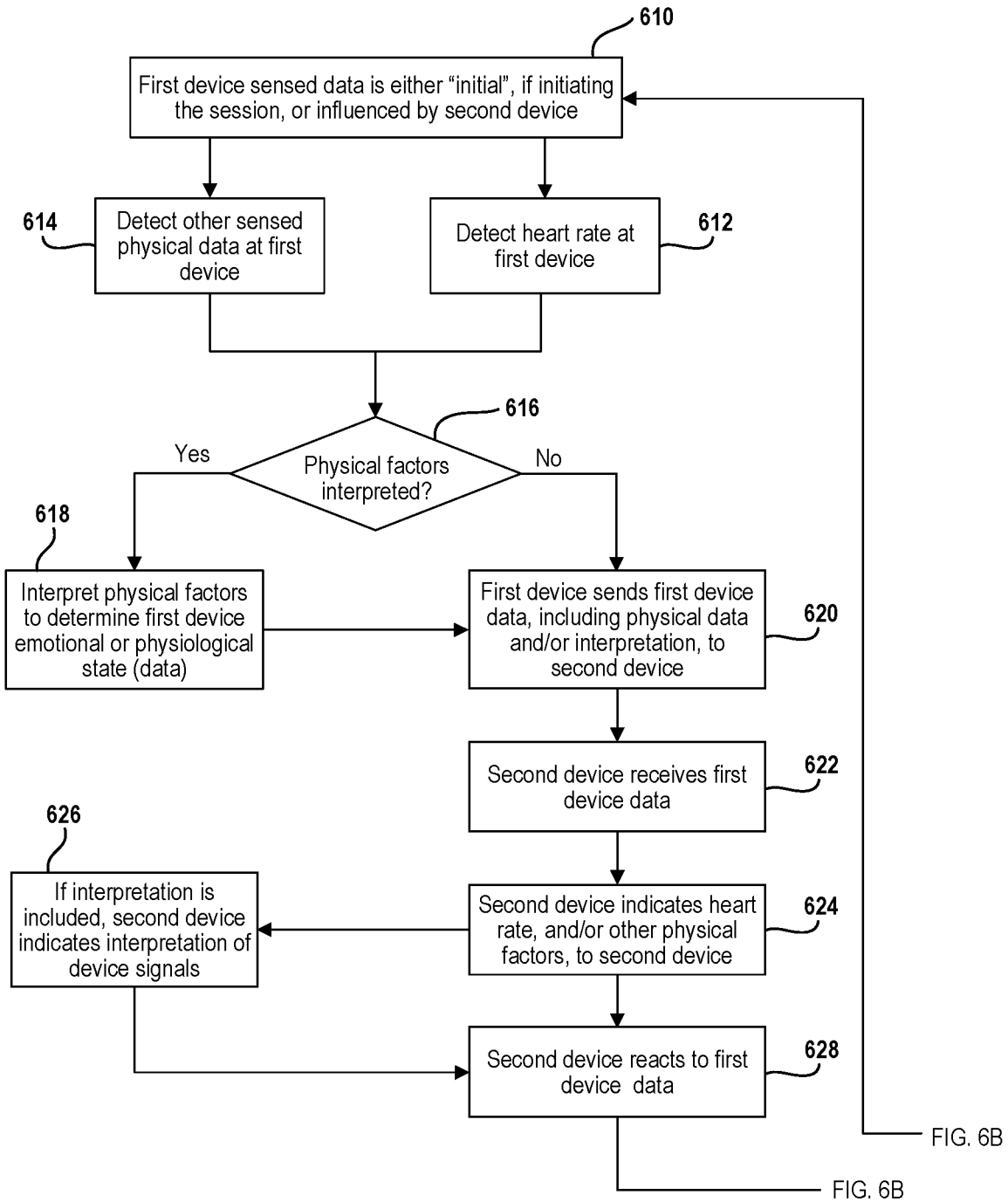
FIGS. 6A and 6B are a continuous flowchart illustrating a method for influencing other fusers.
Figure 6B:
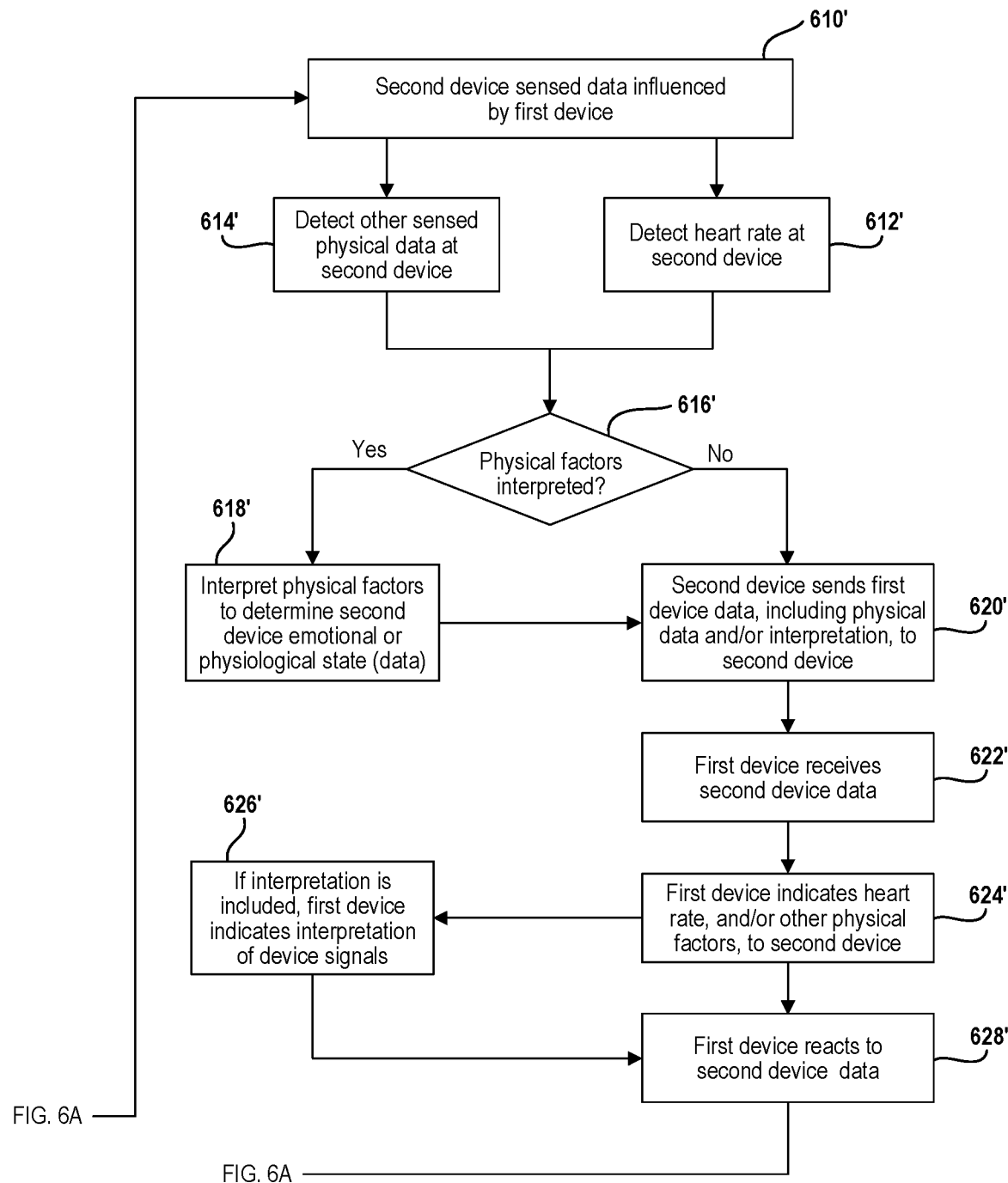

Referring now to FIG. 6, a method for interacting between a first device and a second device is set forth. As will be described in more detail toward the end of FIG. 6, the session may be an initial session or a session that is influenced by another user. In step 610 the session is either started or continued. If continued, the first device and the user associate therewith may be influenced by the signals from the second user device. In step 612 the heart rate is detected at the first device using a physical sensor. In step 614 other sensed physical factors may be detected at the first device. Both heart rate and other sensed conditions are physical factors. However, in some examples only heart rate is used. In other examples heart rate may not be used but other sensed physical data may be determined.

In step 616 the physical factors may be interpreted or passed along as they are. That is, when the physical factors are to be interpreted the heart rate alone or the other sensed physical data or a combination of both may interpreted to determine the emotional or physiological condition of the user of the first device. When the physical factors are not to be interpreted in step 616 step 620 is performed. Step 620 is also performed after step 616. The data corresponding to the emotional or physiological condition in step 618 or the unchanged physical factors are communicated to the second user device. The communication to the second device may take place through the network as described above. Various types of networks and various combinations of networks may be used. In step 622 the second device receives the first device data that may comprise emotional or physiological condition data or the heartbeat data. In step 624 the second device indicates the heart rate and or other physical factors communicated to the second device. In step 626 the interpretation may also be expressed or indicated at the second device. In step 628 the user of the second device reacts to data of the first user? such as the heart rate and physical factors and other interpretation data. The process then repeats but from the perspective of the second user in that the second user then communicates emotional, physiological or physical signals to the first user device. In FIG. 6 the steps 610'-628' are identical expect from the perspective of the second user device relative to the first user device. Therefore the description for the steps are not set forth in further detail.

In operation of FIG. 6, steps 628' and 610' may have a time delayed therebetween so that the physical effects of the conditions of the first user are manifested in the second user. A slight delay such as less than one second may be achieved so that the reaction of the second user may be determined in steps 610'-628'. However, continued communication may also take place. This allows the reaction signal to be observed. The reaction then translates to a change in physical, physiological, and emotional state of second user. The indicators generated by the first device and the second device may continually be changed as each reacts to the other. The various physiological conditions may be happy, sad, lying or the like. The interpretations may present different emojis, colors or other screen indicators corresponding to the different physiological conditions. FIG. 6 is interesting because the first user gets feedback based upon the other user.

Figure 7:
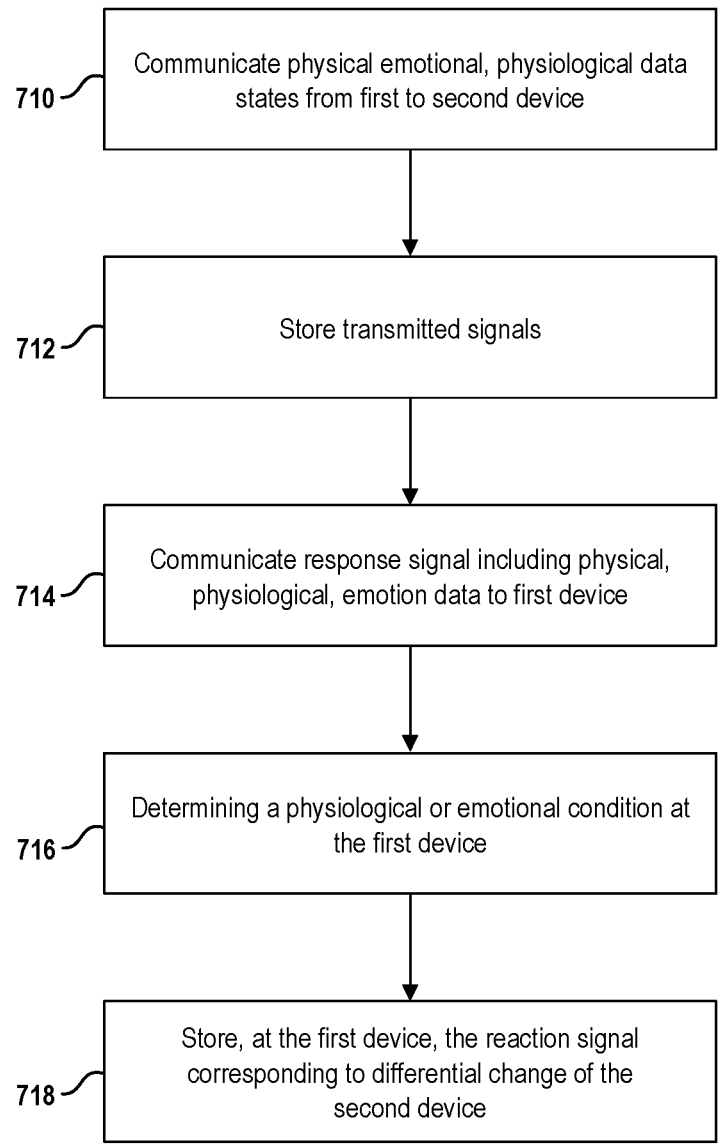
FIG. 7 is a flowchart of a method for storing a response signal.

Referring now to FIG. 7, a method for storing the reaction signal of a second user input from a first user is set forth. In step 710 the physical, emotional or physiological data conditions are communicated from the first device to the second device in a first signal. This is performed in a similar manner set forth in FIG. 6. The transmitted signals are stored in step 712. In step 714 a response signal is generated at the second device. In step 716 the response signal including physiological, physical or emotional data may be communicated to the first device. In step 718 the first device stores the reaction signal corresponding to the differential change of the second device. That is, the reaction or differential change is correlated at the correlation module to the initial stimulus in step 710 based on the elicited response. The change in the response is noted so that, as will be described later, a simulated input may ultimately be communicated to the second user device to elicit a desired response.

Figure 8:
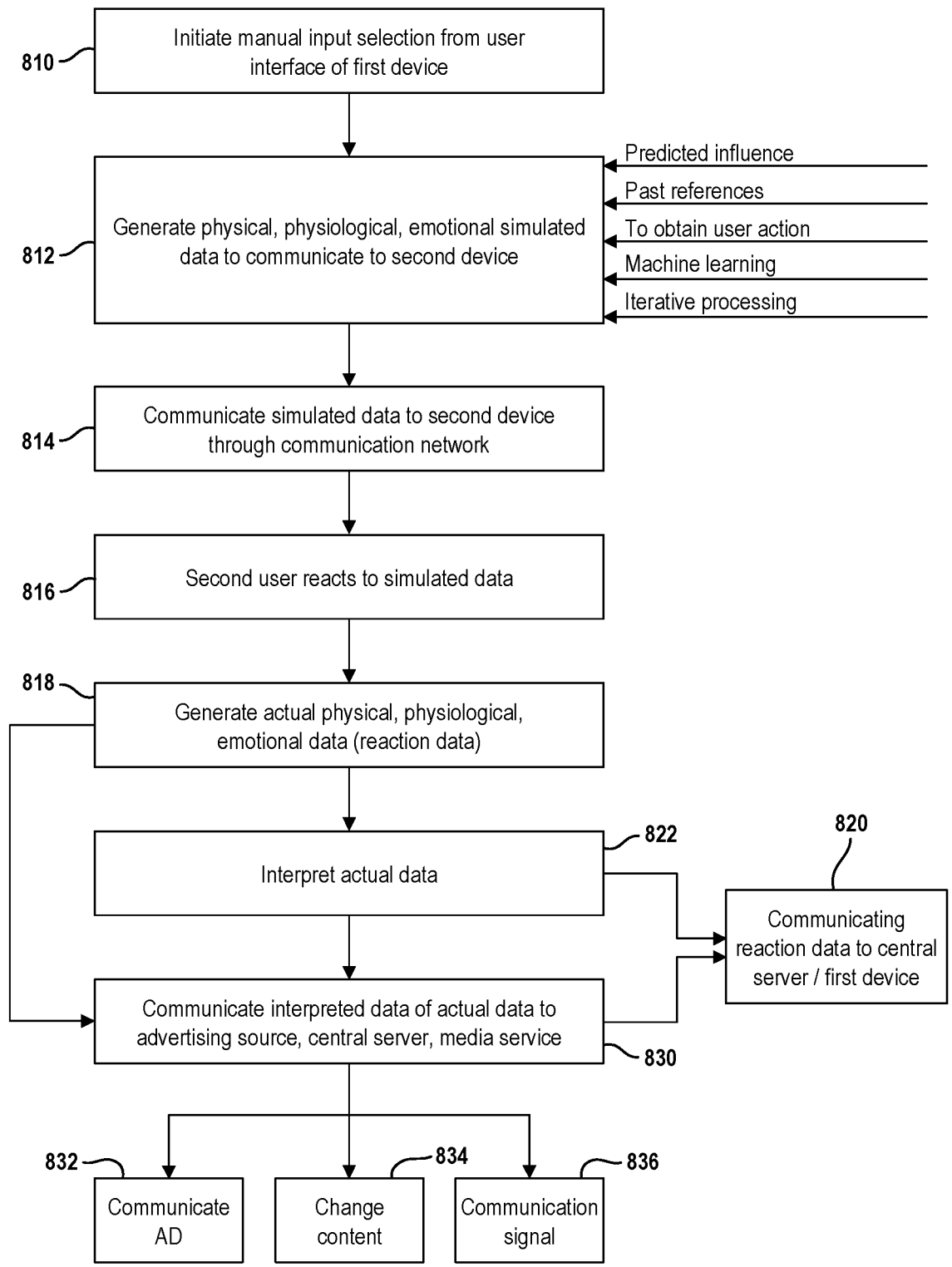
FIG. 8 is a flowchart of a method for providing simulated responses to obtain or elicit a response from another device.

Referring now to FIG. 8, the use of known responses such as those stored in FIG. 7 are set forth. In this example a simulated heart rate, physiological data or emotional data may be provided to another device from a first device or a server acting as the first device. In step 810 the data inputs for the second device are prepared at the first device, which may be the server. The application may provide various options for a type of response desired to be elicited at the second user device. A menu display described below in FIGS. 12A and 12B may be used to select the desired elicited emotion. A server may automatically generate solicited responses. The data referred to in step 810 may be physical data such as a heartbeat, a physiological data and emotional condition. One or combinations of all three may be provided to the second user device. In step 812 the first device data inputs may be modified to elicit a predicted influence or physical, physiological or emotional data from the second user device. The generation of the physiological, emotional or physical simulated data may be performed in response to various types of inputs. The touch data may have a predicted influence based on past reference or past actions. That is, responses may been obtained in a process such as that set forth in FIG. 7. The influence may also be expanded to a user action. That is, the physical, physiological or emotional simulated data may be used to obtain a user action. Machine learning and iterative processing may also be used to modify the simulated data. This process may be performed in real time with a second user device and thus the preface may iteratively approach the desired result at the second user device.

In step 814 the simulated data is communicated to the second user device through the communication network. As mentioned above, the communication network may comprise one or more different types of wired or wireless communication networks. Also the simulated data may also be communicated to a central server to location such as the central server 30 illustrated in FIG. 1. The central server may communicate the simulated data to the second device. In step 816 the user associated with the second device reacts to the simulated data. The reactions may include influencing the second user to perform an action. In step 818 the reaction may include the generation of physical, physiological or emotional data at the second user device. In step 820 the actuated physical, physiological or emotional data may be communicated to a central server or first device for storing the user reaction data therein. The reaction data may comprise the actual physical, physiological or emotional data as well as the simulated data that performed or obtained the reaction. In this way a delta may be formed so that in the future the simulated data may be modified to be closer to the desired response.

In step 822 the actual data generated in step 818 may be interpreted. The interpreted data may also be stored within the central server or the first device for similar reasons set forth above. That is, the interpreted data may demonstrate the particular response or intensity of the response. Of course, the populations of users may be influenced by obtaining data from multiple users in response to simulated data. After step 818 and 822 one or both of the actual data or the interpreted data from steps 818 and 822 may be communicated to an advertising source, a central server or a media source in step 830. By obtaining the actual data or interpreted data the different servers or sources may communicate an advertisement based upon the data in step 832. The content may also be changed in response to the actual or interpreted data. That is, a user watching a program or being streamed programming may have the programming changed to better fit the physical, physiological or emotional data. The communicated ad in block 832 may also be communicated to better fit the data. If the desired content or desired advertising is desired to be viewed or acted upon by a user, the simulated data may be provided to elicit a certain emotion or mood so that the user may be more receptive to the communicated ad or the content. By way of example, if the user is watching a professional basketball player and the basketball player dunks, additional media content of basketball highlights may be provided to the second user if the reaction to the dunk was positive. A reaction may, for example be "happy" or "exuberant" or "impulsive" in physiological or emotional state, or in a physical state that corresponds to such physiological or emotional states Likewise, advertisements for certain brands of sneakers that are worn by the basketball player may be communicated.

A communication signal in block 836 may also be communicated to a central server. Feedback may be provided to the basketball player, who may then change the intensity of their dunks, the angles from which they dunk, or other actions in order to elicit an even more positive result at the second user, a result more consistent with the desired response by the second user Likewise, the communication signals may be communicated to the second user by way of text, e-mails or other electronic means.

The system may also be used as a dating application. A spiking heart rate, with high intensity, of a man may be simulated, or their excited or attracted emotional or physiological state may be simulated, side by side with their profile photo or video or description, in order to elicit attraction by the woman to such man. A spiking heart rate, with high intensity, of a man may be simulated, or their excited or attracted emotional or physiological state may be simulated, side by side with their profile photo or video or description, in order to elicit attraction by the woman to such man. Then, a woman may view a video profile of such man. A physical, physiological, or emotional state of the woman, in response to the combination of the simulated states of the man and the profile of the man, may then be measured in order to indicate an attraction to certain characteristics which may be recorded at a central server so that profiles of other men of the same characteristics may be provided to the woman.

Another example is a villain of a horror reality show in which the villain may choose to, based upon a reaction of the viewing audience, hold off doing a scary act as an escalating level of suspense. The villain may be instructed to continue to build up suspense until an optimal time when a certain level of the audience is in a suspenseful or physiological state.

The communication signal 836 may be communicated through a video game to provide certain rewards or notifications. Promotional items in a video game fall under communicating an ad in block 832.

Figure 9A:
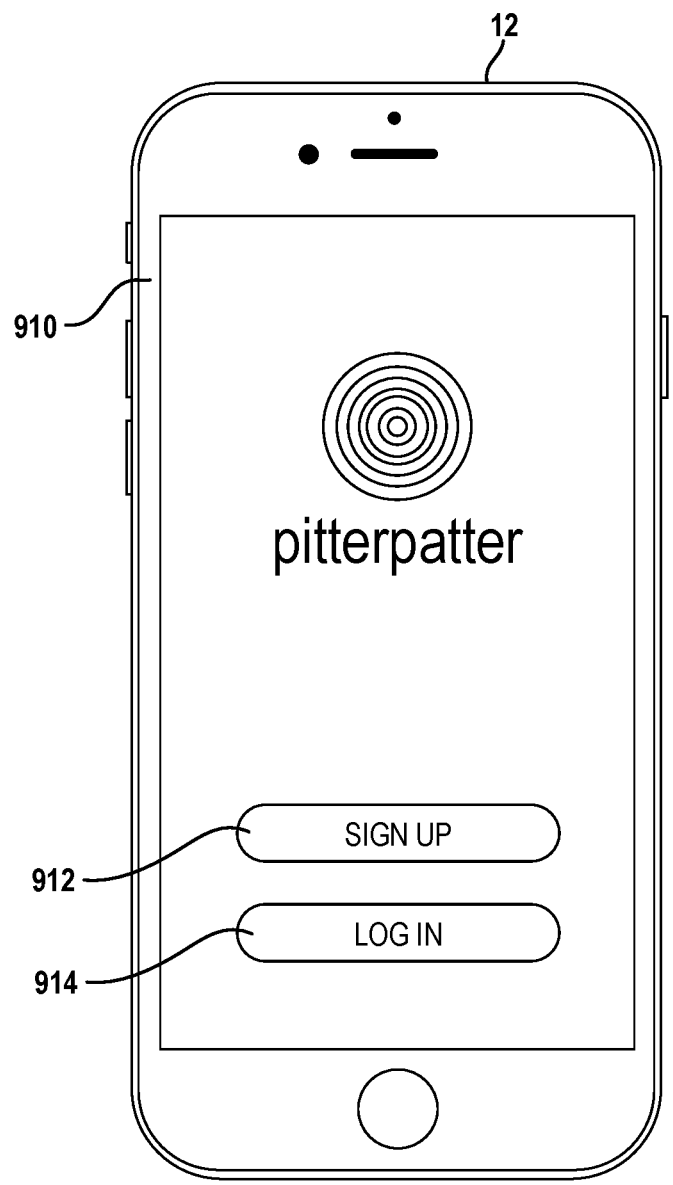
FIG. 9A is a user device having a screen display for signing up or logging into the system.

Referring now to FIG. 9A, the user device 12 is illustrated. The user device 12 includes a screen display 910 for signing up or logging into the system. Signing up for the service may allow various data to be stored at the central server such as a user device being associated with a particular user. This is performed by selecting the button 912.

By selecting button 914 a user may log in using an already determined password or other type of user authentication such as a retina scan or fingerprint. Logging in allows a user to access various screen displays.

Figure 9B:
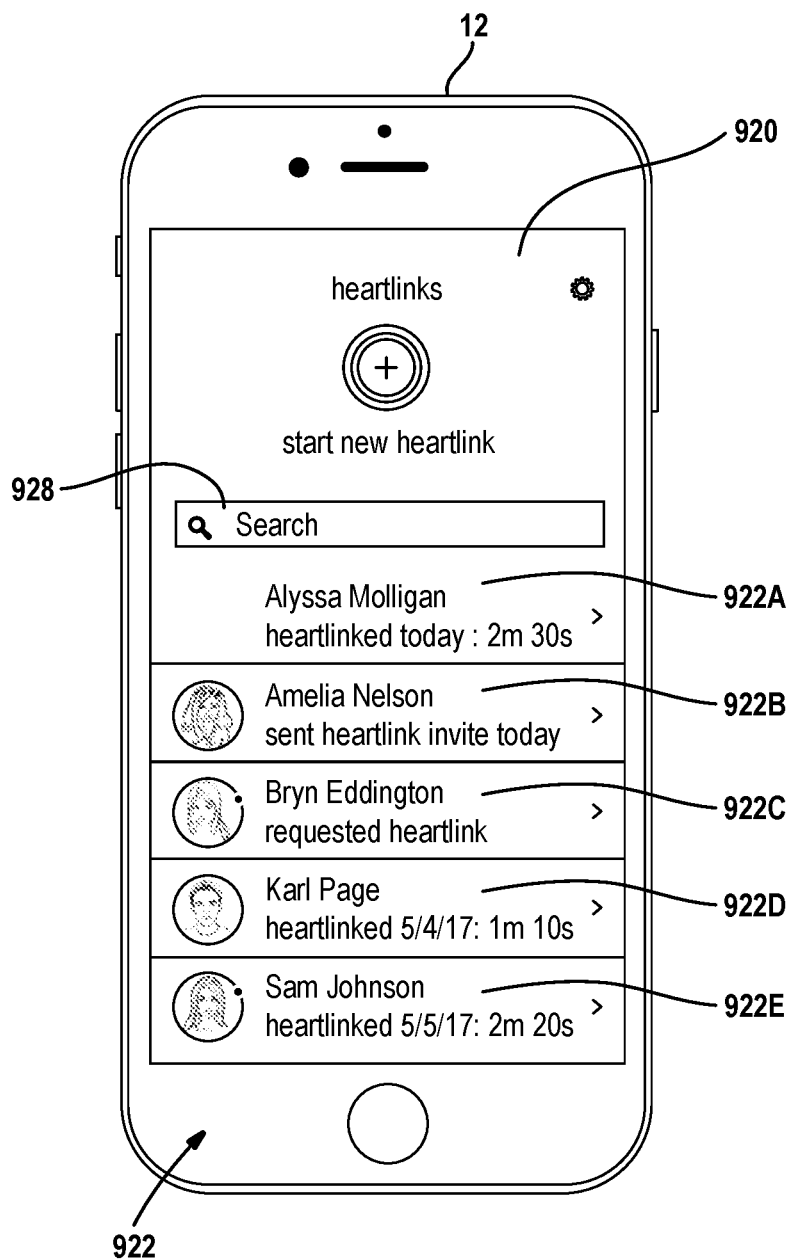
FIG. 9B is a screen display illustrating a way to start a link.

Referring now to FIG. 9B, the user device 12 is illustrated having a screen display 920. The screen display 920 is reached after the user signs in or logs in with reference to FIG. 9A. The screen display 920 includes a plurality of users in a user history 922. A user history provides communications received from or provided by the user device 912 relative to the application. The first line of the user history shows heart link was activated for "Alyssa Molligan" for two minutes and thirty seconds. History 922B describes "Amelia Nelson" communicating an invitation for linking earlier in the day. History 922C shows "Brinn Eddington" requesting a heart link. The fourth and fifth lines 922D and 922E show past linking sessions and the times and dates associated therewith. By selecting by one of the lines within the history 922, a quick link may be used to form a request for a new heart link to another user.

A search box 928 may also be provided. The search box 928 may allow a user to enter a name for searching for a particular user to reach out and heart link.

Figure 9C:
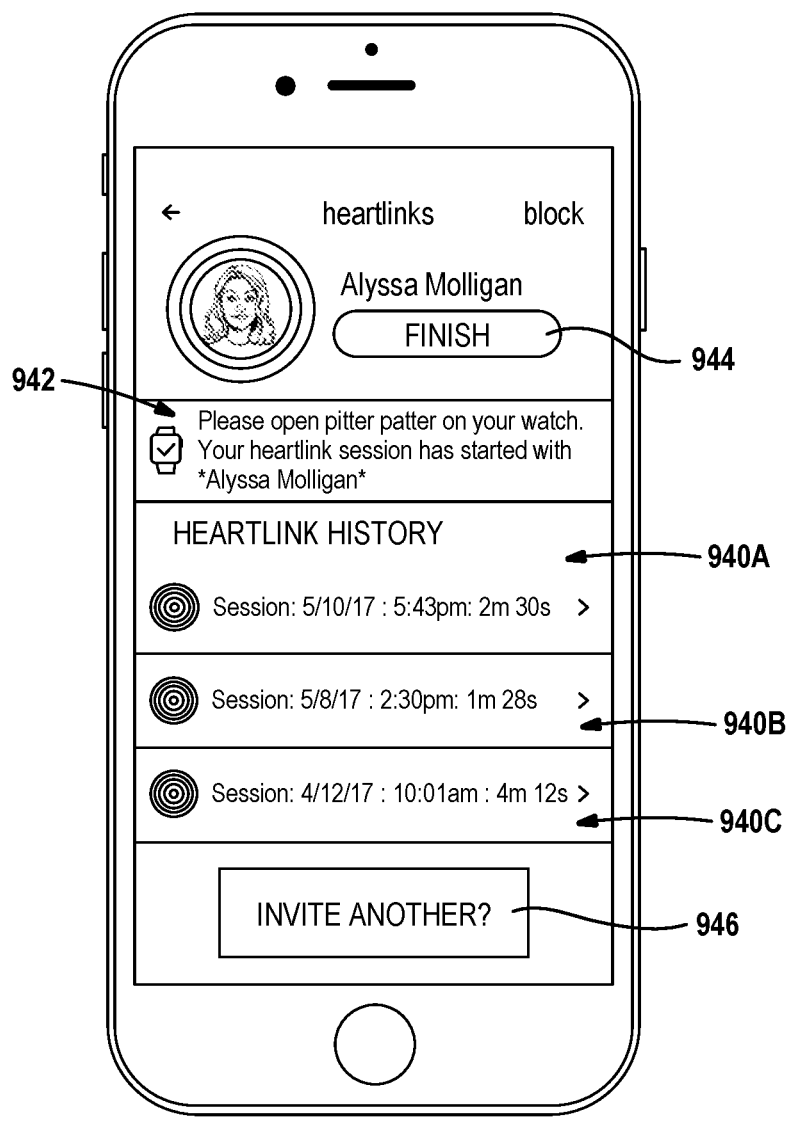
FIG. 9C is a screen display providing instructions for starting a linking session.

Referring now to FIG. 9C, when a user history 922A is selected a new heart link session may be opened. In this example prior sessions with the particular user selected may be provided in the history portion 940A-940C. As can be seen, the most recent event that was displayed in FIG. 9B is displayed at the top of the heart link history at line 940A.

In this example, an instruction portion 942 is provided. The instructions portions provide instructions to a user to start a companion (watch) application to start the heart link session. To end a heart link session button 944 may be selected. Once the application on the companion device such as a watch is initiated a session may be formed. The session may be easily expanded to more than one person by selecting the "invite another" button 946. Thus more than one user may be provided content from the user device 12.

Referring now to FIG. 10A, a broadcasting type method may also be initiated. The heart link session may provide a live feed to many people that have the option to join. The screen display 1010 includes a plurality of users 1012A, 1012B and 1012C that are currently generating live feeds. Each user is represented by a thumbnail or icon 1012A, 1012B and 1012C that may also act as a user interface button for selecting joining a live feed. The screen display 1010 may also include a session initiation button 1014 may activate or initiate a live session from the user device to many user devices. The starting of the session may communicate an identifier to various users as described above. The initiation of a live session may also be advertised by the central server. That is, the user may have the option to only start a session with a known group of friends, relatives or the like. However, various celebrities may choose to have a live session capable of being joined by any party. A history portion such as a one-to-one history 1016 may be generated as well as a one-to-many history 108 which, when selected may provide the user with a respective one-to-one history or one-to-many history for the user device.

A search box 1020 may be used to search for various live sessions or various users to start a session.

Referring now to FIG. 10B, once the session initiation button 1014 is selected the screen display 1030 may be initiated. The screen display 1030 may provide a confirmation button 1032 labeled "start" in this example for starting a live heart link. As mentioned above other users may be restricted from joining. However, other users may not be restricted and a public session may be started. A picture of the user associated with the user device 1034 may be illustrated as well. Thumbnails of various users associated with the live session may be generated by the indicators 1036.

Figures 10C, 10D:
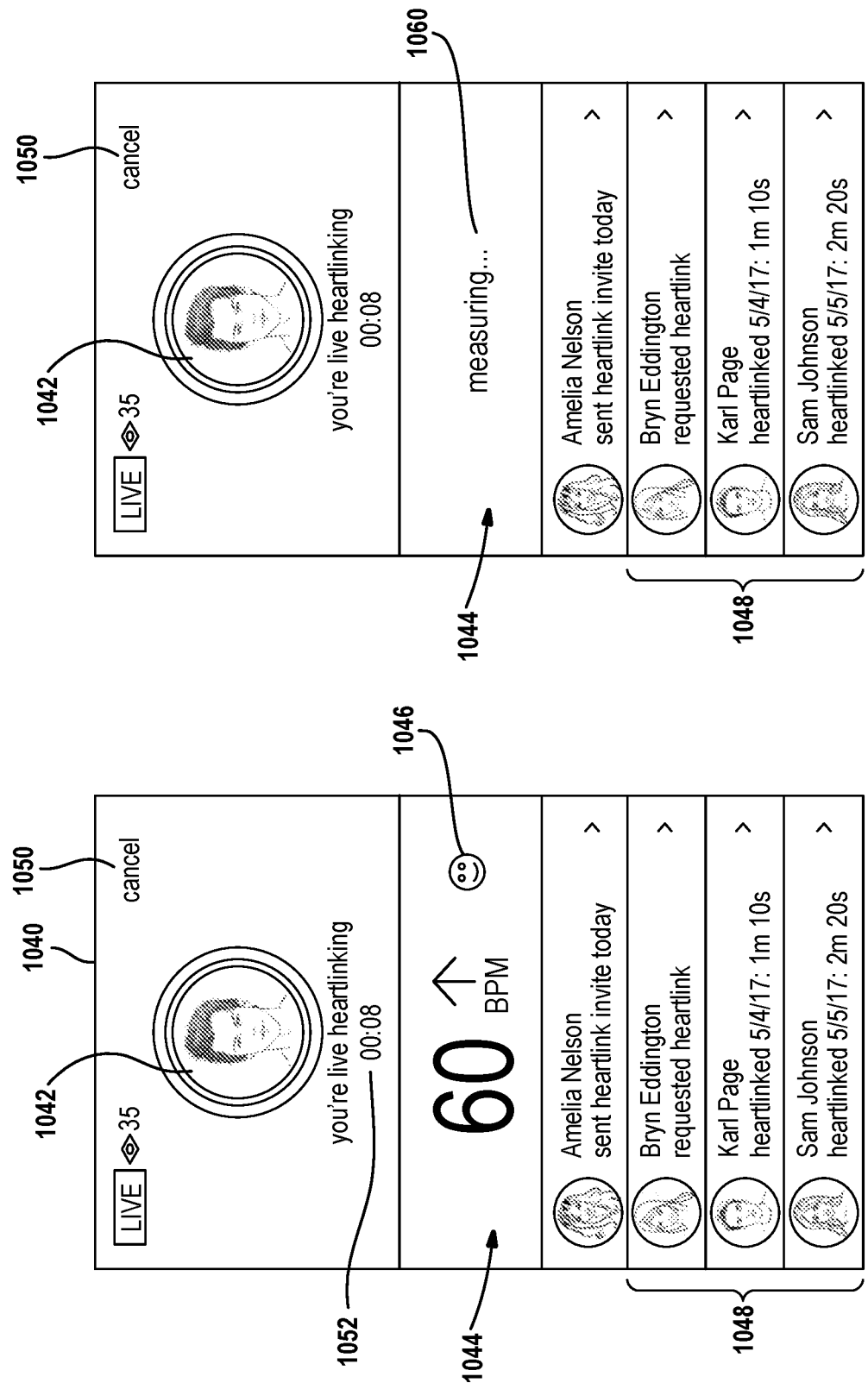
FIG. 10C is a screen display during a live session.
FIG. 10D is a screen display during the measuring process.

Referring now to FIG. 10C, once a live session is initiated a "touch data" portion 1044 may be set forth. The touch data portion 1044 may include physical data, physiological condition data, or emotional condition data. In this example, physical condition data such as sixty beats per minute are displayed as well as an emoji 1046 to correspond to an emotional condition. A history portion 1048 may also be displayed. A cancel button 1050 may also be provided to cancel the live session on the screen display 1040. A clock 1052 may also be provided to show the amount of time that the live session has been active.

Referring now to FIG. 10D, when the portion 1044 is changing, a "measuring" display 1060 may be displayed to indicate the system is measuring the physical condition, physiological condition or emotional condition of the user.

Referring now to FIG. 11A, the process may also be initiated at a companion device 14. The companion device 14 has a screen display 1110 that provides a plurality of users 1112A, 1112B, 1112C, 1112D and 1112E. Referring now to FIG. 11B, when one of the users such as the user associated with 1112A is selected, screen display 1120 provides an initiation screen for initiating a session with a particular user by activating a start button 1122.

Referring now to FIG. 11C, a screen display 1130 may be generated. To finish the session, the finish button 1132 may be selected. During the session, a name indicator 1134, a picture 1136 and a physical data 1138 may be displayed. An emoji 1150 may also be displayed. The emoji may correspond to the current emotional condition of the user. An increasing or decreasing indicator 1152 may correspond to the increasing or decreasing of the heart rate indicator 1138.

Referring now to FIG. 12A, a screen display 1210 is illustrated for starting a simulation session. To start a simulation session, a button 1212 may be selected. The button 1212 may initiate the activation of the screen display 1220 in FIG. 12B. The screen display in 12B display a plurality of desired responses by the buttons 1222, 1224, 1226 and 1228. A scroll area 1230 may be used to scroll down for further options. In this example, button 1212 corresponds to the desired responses of happy. Button 1224 corresponds to the desired response of excited. Button 1226 corresponds to the desired response of sad. Button 1228 corresponds to the desired button of comforted. Upon selecting one of the buttons, a simulated response may be communicated from the first user device to a second user device. The simulation may include simulated data for a physical response, such as a simulated heartbeat, an emotion condition data to provide an indicator of emotion or a physiological condition indicator to illustrate a physiological change. Of course, combinations of simulated physical, physiological and emotional conditions may be used. Once selected, a simulated response selection signal corresponding to the desired simulated response is used to trigger the communication of a physical conditional signal, an emotional condition signal or a physiological conditional signal or a combination thereof.

Those skilled in the art can now appreciate from the foregoing description that the broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification and the following claims.

The invention claimed is:

1. A method comprising:
   authenticating a first device at a central server;
   authenticating a second device at the central server;
   authenticating a third device at the central server;
   after authenticating the first device, initiating a live session at a first device having a session identifier, said live session being one-to many, said first device being associated with a first user;
   storing session forming data at the central server;
   communicating the session identifier to a second device associated with a second user and a third device associated with a third user through a network;
   after authenticating the second device and authenticating the third device, joining the live session with the third device based on input from a user interface of the third device and the session identifier and joining the live session with the second device based on input from a user interface of the second device and the session identifier;
   generating a physical condition signal at a physical condition sensor;
   converting the physical condition signal to a first signal;
   communicating, based on the live session, the first signal to the second device through the network and the third device through the network;
   generating, in real time, a haptic indicator at the second device and the third device corresponding to the first signal.

2. The method of claim 1 wherein initiating the live session comprises selecting the second device from an associated list comprising users associated with the first device.

3. The method of claim 1 wherein initiating the live session comprises broadcasting the session identifier to the second device and the third device through the central server.

4. The method of claim 1 further comprising communicating the session identifier to the second device and a third device using at least one of an email, a text message and an application notification.

5. The method of claim 1 wherein the physical condition sensor comprises a heartbeat sensor or a galvanic sensor.

6. The method of claim 1 further comprising interpreting a physiological condition or an emotional condition at the central server from the physical condition signal.

7. The method of claim 1 further comprising interpreting a physiological condition or an emotional condition at the first device from the physical condition signal.

8. The method of claim 7 wherein interpreting the physiological condition or emotional condition comprises interpreting the physiological condition or the emotional condition from a user selectable input and the physical condition signal.

9. The method of claim 7 wherein interpreting the physiological condition or emotional condition comprises detecting a physical condition from a physical condition sensor of a companion device coupled to the first device.

10. A method comprising:
    authenticating a first device at a central server;
    authenticating a second device at the central server;
    after authenticating the first device;
    after authenticating the first device, initiating a live session at the first device, said live session comprising a session identifier, said first device being associated with a first user;
    storing session forming data at the central server;
    communicating the session identifier to the second device through a network, said second device associated with a second user;
    after authenticating the second device, joining the live session from the second device;
    determining, at the first device, a first condition corresponding to a first physical condition, a first physiological condition, a first emotional condition or combinations thereof;
    converting the first condition to a first signal;
    communicating, based on the live session, the first signal to the second device through the network;
    receiving the first signal at the second device;
    generating, in real time, a first haptic indicator at the second device corresponding to the first signal;
    determining, at the second device, a second condition corresponding to a second physical condition, a second physiological condition, a second emotional condition or combinations thereof in response to the first indicator;
    converting the second condition to a second signal;
    communicating, based on the live session, the second signal to the first device through the network;
    receiving the second signal at the first device; and
    generating, in real time, a second haptic indicator at the first device corresponding to the second signal.

11. The method of claim 10 further comprising interpreting the first physiological condition or the first emotional condition from the first physical condition.

12. The method of claim 10 further comprising interpreting the first physiological condition or the first emotional condition at the first device from the first physical condition and a user selectable input.

13. The method of claim 10 further comprising interpreting the first physiological condition or the first emotional condition at the first device from a physical condition sensor of a companion device coupled to the first device.

14. A method comprising:
    authenticating a first device at a central server;
    authenticating a second device at the central server;
    after authenticating the first device;

after authenticating the first device, initiating a live session at the first device, said live session comprising a session identifier, said first device being associated with a first user;

storing session forming data at the central server;

communicating the session identifier to the second device through a network, said second device associated with a second user;

after authenticating the second device, joining the live session using a user interface of the second device;

selecting a desired response to elicit from a second user of the second device from a user interface of the first device to form a selection signal;

converting the selection signal into a first signal corresponding to a physical condition, a physiological condition, an emotional condition or combinations thereof based on the desired response;

communicating, based on the live session, the first signal to the second device through the network; and generating, in real time, a haptic indicator at the second device corresponding to the first signal.

15. The method of claim 14 further comprising communicating a response signal from the second device corresponding to the first device through the network.

16. The method of claim 15 further comprising comparing the desired response to the response signal to obtain a correlation and storing the correlation at the first device.

17. The method of claim 16 further comprising selecting a second desired response to elicit from the second user of the second device from the user selectable input of the first device to form a second selection signal;

converting the second selection signal into a second signal corresponding to a physical condition, a physiological condition, an emotional condition or combinations thereof based on the second desired response and the correlation.

18. The method of claim 14 wherein selecting the desired response is subnormal.

19. A method comprising:

authenticating a first device at a central server;

authenticating a second device at the central server;

after authenticating the first device;

after authenticating the first device, initiating a live session at the first device, said live session comprising a session identifier, said first device being associated with a first user;

storing session forming data at the central server;

communicating the session identifier to the second device through a network, said second device associated with a second user;

after authenticating the second device, joining the live session using a user interface of the second device;

determining, at the second device, a first condition corresponding to a first physical condition, a first physiological condition, a first emotional condition or combinations thereof in response to a first input;

converting the first condition to a first signal;

communicating, based on the session data, the first signal to the first device through the network and to a server associated with the live session;

receiving the first signal at the server device; and performing, in real time, an action at the server device in response to the signal.

20. The method of claim 19 wherein performing the action comprises communicating a push notification to the second device.

21. The method of claim 19 wherein performing the action comprises communicating feedback to the second device from the server and generating a visual indicator, an audible indicator or a haptic indicator at the second device.

22. The method of claim 19 wherein performing the action comprises aggregating responses from a plurality of users at the server.

23. The method of claim 19 wherein performing the action comprises communicating an advertisement.

24. The method of claim 19 wherein performing the action comprises communicating a text message.

25. The method of claim 19 wherein the first device comprises the server.

26. The method of claim 19 wherein the first input is a simulated physical condition, a simulated physiological condition or a simulated emotional condition.

27. The method of claim 19 wherein the first input is from a trigger source.

* * * * *